(12) United States Patent
Hedberg et al.

(10) Patent No.: US 7,908,005 B2
(45) Date of Patent: Mar. 15, 2011

(54) MEDICAL SYSTEM FOR MONITORING AND LOCALIZATION OF ELECTRODE LEADS IN THE HEART

(75) Inventors: Sven-Erik Hedberg, Kungsängen (SE); Kenth Nilsson, Åkersberga (SE)

(73) Assignee: St. Jude Medical AB, Jarfalla (SE)

( * ) Notice: Subject to any disclaimer, the term of this patent is extended or adjusted under 35 U.S.C. 154(b) by 178 days.

(21) Appl. No.: 12/294,268

(22) PCT Filed: Mar. 27, 2006

(86) PCT No.: PCT/SE2006/000384
§ 371 (c)(1),
(2), (4) Date: Sep. 24, 2008

(87) PCT Pub. No.: WO2007/111542
PCT Pub. Date: Oct. 4, 2007

(65) Prior Publication Data
US 2009/0287269 A1    Nov. 19, 2009

(51) Int. Cl.
*A61N 1/365* (2006.01)
(52) U.S. Cl. ........................................................ 607/17
(58) Field of Classification Search ................. 607/9, 17
See application file for complete search history.

(56) References Cited

U.S. PATENT DOCUMENTS

| | | | | |
|---|---|---|---|---|
| 4,124,031 A | * | 11/1978 | Mensink et al. | 607/31 |
| 4,898,181 A | | 2/1990 | Kessler | |
| 5,792,194 A | * | 8/1998 | Morra | 607/17 |
| 5,846,198 A | | 12/1998 | Killmann | |
| 6,574,498 B1 | | 6/2003 | Gilboa | |
| 6,990,370 B1 | | 1/2006 | Beatty et al. | |
| 2004/0059237 A1 | | 3/2004 | Narayan et al. | |
| 2004/0254437 A1 | | 12/2004 | Hauck et al. | |

FOREIGN PATENT DOCUMENTS

| | | |
|---|---|---|
| EP | 0 775 466 | 5/1997 |
| EP | 1 023 870 | 8/2000 |
| WO | WO 99/39650 | 8/1999 |
| WO | WO 99/52430 | 10/1999 |

* cited by examiner

*Primary Examiner* — Carl H Layno
*Assistant Examiner* — Brian T Gedeon
(74) *Attorney, Agent, or Firm* — Schiff Hardin LLP

(57) ABSTRACT

A medical system has an implantable heart stimulator with sensing and stimulating pairs of electrodes, with an electric field through the heart being generated by the respective pairs by the application of alternating voltages at a preset frequency to the respective pairs. A signal receiver receives a signal representing the voltage potential difference between the voltage potential at one of the electrodes in the pair, and a reference electrode. The detected voltage is related to the generated electric field, and the signal receiver generates a potential different signal that is supplied to a control unit to determine parameters therefrom representing cardiac activity.

18 Claims, 4 Drawing Sheets

MEDICAL SYSTEM FOR MONITORING AND LOCALIZATION OF ELECTRODE LEADS IN THE HEART

BACKGROUND OF THE INVENTION

1. Field of the Invention

The present invention relates to a medical system for monitoring and localization of electrode leads in the heart.

Generally the present invention is applicable to obtain information about hemodynamic heart activity, e.g. related to heart wall movements, heart wall thickening or valve plane movement. This obtained information is then used to improve the setting of an implantable heart stimulator.

The present invention is in particular applicable to identify optimal settings of AV- and/or VV-delays in an implantable heart stimulator, and to identify optimal electrode positions within the heart and in the coronary heart vessels. The invention may be used both during implantation procedures and at follow-up procedures.

2. Description of the Prior Art

AV- and VV-delay are important hemodynamic parameters that need to be individually set for every patient and electrode position. The optimal settings of AV- and VV-delay need feedback from data disclosing the hemodynamic status at different AV/VV-delay settings. This can be performed by measuring the blood flow in the heart with e.g. ultrasound equipment. However, such equipment is normally not available during implantation of pacemakers and implantable cardioverters/defibrillators (ICDs).

In the mapping system of Endocardial Solutions three electric fields are created in the thorax of a patient by applying alternating currents between pairs of cutaneous electrode patches. The patches are arranged to let currents through the patient to be almost perpendicular to each other. The currents are time multiplexed in order to obtain only one electric field at a time. A catheter, provided with sensing electrodes, and inserted into the thorax region, e.g. inside the heart, will experience a voltage which will depend upon the projection of the electrode on the axis being parallel to the electric field. The collected information from the catheter is used to track or navigate the movement of the electrodes and to construct a three-dimensional model of the heart chambers.

SUMMARY OF THE INVENTION

Primary objects of the present invention are to obtain information that may be used a) to optimize time intervals of an implantable heart stimulating device, e.g. the AV-/VV-intervals; and b) to identify optimal positions for heart electrodes, preferably during the implantation procedure.

The above object is achieved in accordance with the present invention by a medical system for use with an implantable heart stimulator having a number of sensing and stimulating heart electrodes organized in electrode pairs, that generate an electric field through the heart between electrodes of respective pairs, by applying excitation signals to the electrodes at a predetermined frequency. A signal receiver receives a signal representing the voltage potential difference between at least of the electrodes, used as a detecting electrode, and a reference electrode. The voltage potential is related to the generated electric field and a potential difference signal is generated therefrom that is used to determine parameters representing cardiac activity.

Thus, the present invention is based upon a system similar to the above-mentioned system from Endocardial Solutions. The system according to the present invention may be a part of, or may be connected to, a programmer for a pacemaker or an ICD to be used in connection with implantation of a pacemaker or an ICD system, or during follow-up procedures of such devices. As an alternative, the device may be a incorporated in a pacemaker or an ICD system.

The present invention is especially applicable to a situation when leads and catheters are to be inserted or applied to the heart. However, other scenarios are possible. External patches attached to thorax of a patient with an implanted pacemaker/ICD system may be used in the same way as described above. Measuring voltages will be applied between pairs of patch electrodes. The implanted system is provided with circuitry that amplifies the voltages induced by the measurement current in body tissue between the pacemaker electrodes and to transmit these data to an external unit, in real time or later via data stored in the unit.

Using the external patches for obtaining orthogonal electric fields, measurements between the pacemaker can and the implanted electrodes will be achieved, unless electrodes are positioned in thorax for the purpose of collecting signals from more than the pacemaker can—lead electrode vector orientation. This vector orientation may be used for comparative measurements over time. The three patch electrode pairs are used to detect the voltage differences in each electric field direction, i.e. the projection of the potential difference in each direction.

The first measurement is preferably performed during implantation and then at each follow-up.

A gradually decreasing contractility could be followed by the measurements of the voltage variations projected on the can/electrode vector.

The time switching, multiplexing, of the electric fields may be used also here. There may however be a delay between sensed signals and corresponding data sent out to the external unit. This may be overcome by registering of signals for one field orientation at a time for at least a whole heart cycle. Pattern recognition may then be applied to identify which multiplexing phase that belongs to which electric field.

According to another alternative embodiment the electric field(s) is/are being created within the body of the person carrying a device according to the present invention.

In the figures similar or the same features have the same references signs in all figures.

DESCRIPTION OF THE PREFERRED EMBODIMENTS

Figure 1:
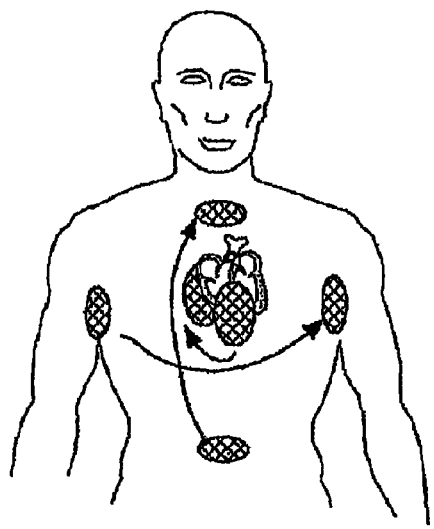
FIG. 1 schematically illustrates an arrangement of electric field generating electrodes, applicable in the present invention.

FIG. 1 shows how the patches may be arranged to setup three orthogonal electrical fields, and also an alternating voltage applied between pairs of patches. The pacemaker leads are not shown in FIG. 1.

Figure 2:
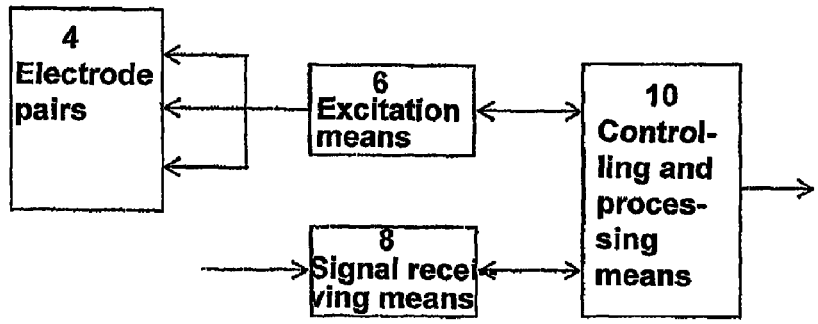
FIG. 2 shows a simplified block diagram of a medical system according to the present invention.

FIG. 2 shows a simplified block diagram of a medical system according to the present invention.

Figure 3:
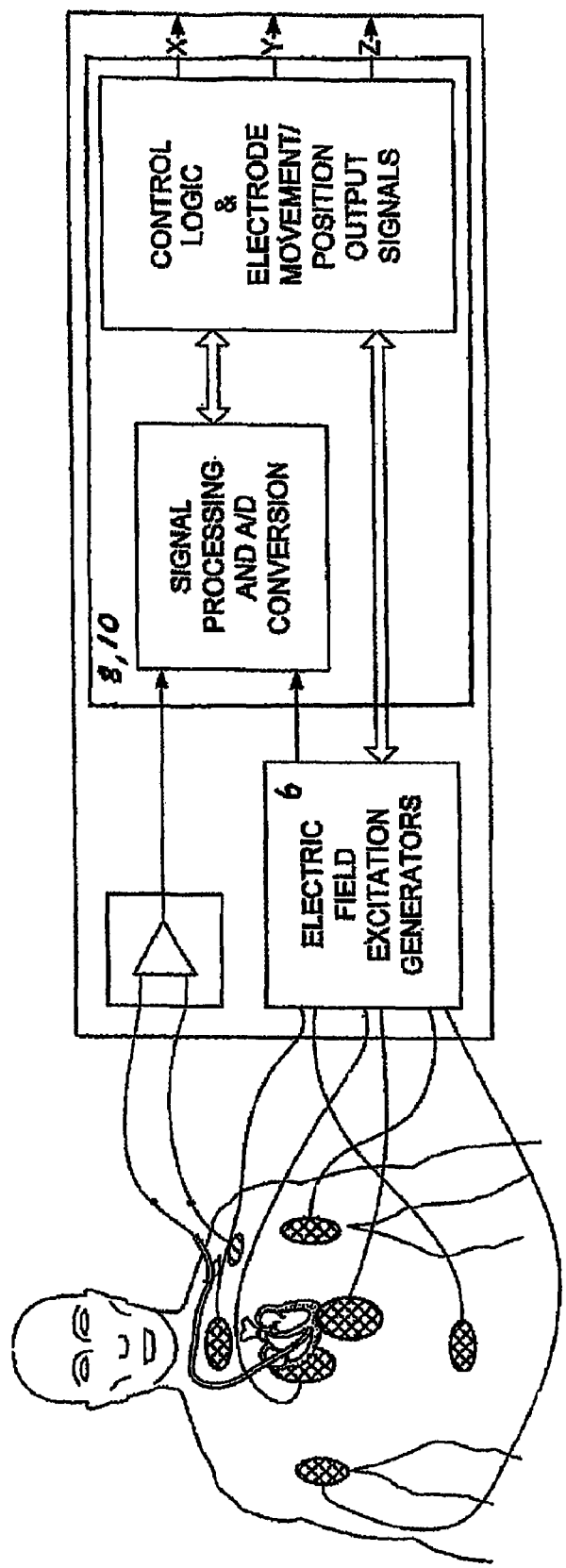
FIG. 3 shows a block diagram of the medical system according to the present invention.

With references in particular to FIG. 2, but also to FIGS. 3 and 4 the medical system will now be described. The medical system is to be used in connection with an implantable heart stimulator that is provided with sensing and stimulating heart electrodes.

The system has a predetermined number of electrode pairs 4 to be arranged at or within a human being or animal such that an electric field through the heart may be generated between the electrodes of respective electrode pair. According to a preferred embodiment three electrode pairs, e.g. surface patch electrodes, are arranged, preferably in an orthogonal arrangement as indicated in FIG. 1. The electric field(s) is/are generated by an excitation unit 6, including electric field excitation signal generators, connected to the electrodes, by applying alternating voltages, or alternating currents, at a preset frequency to the electrodes of the electrode pair(s).

The system further comprises a signal receiving unit 8 that receives a signal representing the voltage potential difference between the voltage potential of at least one of the heart electrodes used as detecting electrode and the voltage potential at a reference electrode. The voltage potential is related to the generated electric field. The signal receiving unit 8 then generates a potential difference signal that is applied to a signal controlling and processing unit 10 that processes the detected potential difference signal in order to determine parameters representing heart activity. With references to FIGS. 3 and 4 the excitation unit 6 includes a first switch that, under the control of the controlling and processing unit 10, switches between electrode pairs such that the generated electrical fields from different electrode pairs are generated separate from each other. The signal receiving unit 8 includes a second switch (see FIGS. 3 and 4) adapted to perform, also under the control of the controlling and processing unit 10, a switching in synchronism with the switching of the first switch such that a correlation between the received voltage potential difference signal and the respective electric field generating electrode pair is achieved.

As indicated above, and in order to further increase the accuracy of the measurements, more than one of the heart electrodes may be used as detecting electrode. In that case, a further switching means (not shown) is arranged to switch, under the control of the controlling and processing unit 10, between the different detecting electrodes when each of the electric field generating electrode pair is active. In particular this may be advantageous during measurements of movements of the heart valve plane.

The alternating voltage applied to the electric field generating electrodes are sequentially distributed to the three pairs of surface electrodes and the alternating voltage preferably has a square wave pulse form and a frequency in the interval 1-10 kHz. Those skilled in the art are naturally aware of other appropriate pulse forms, e.g. a sinus shaped pulse form, that may be used.

When using the medical system during an implantation procedure the signal receiving means is adapted to be directly connected to the electrode lead(s) of the heart stimulator and/or to the heart stimulator and is then adapted to receive signals from electrodes at the electrode lead(s) and also to receive signals from an electrode surface at the heart stimulator housing.

When using the medical system during a follow-up procedure the voltage potential difference sensed by the heart stimulator electrodes instead are wirelessly transferred from the implantable stimulator to the signal receiving means using conventional telemetry technique.

The signal receiving unit 8 includes sample and hold circuits activated in dependence of the generated alternating voltages to generate a slowly varying signal representing the movement of the detecting electrode.

Figure 4:
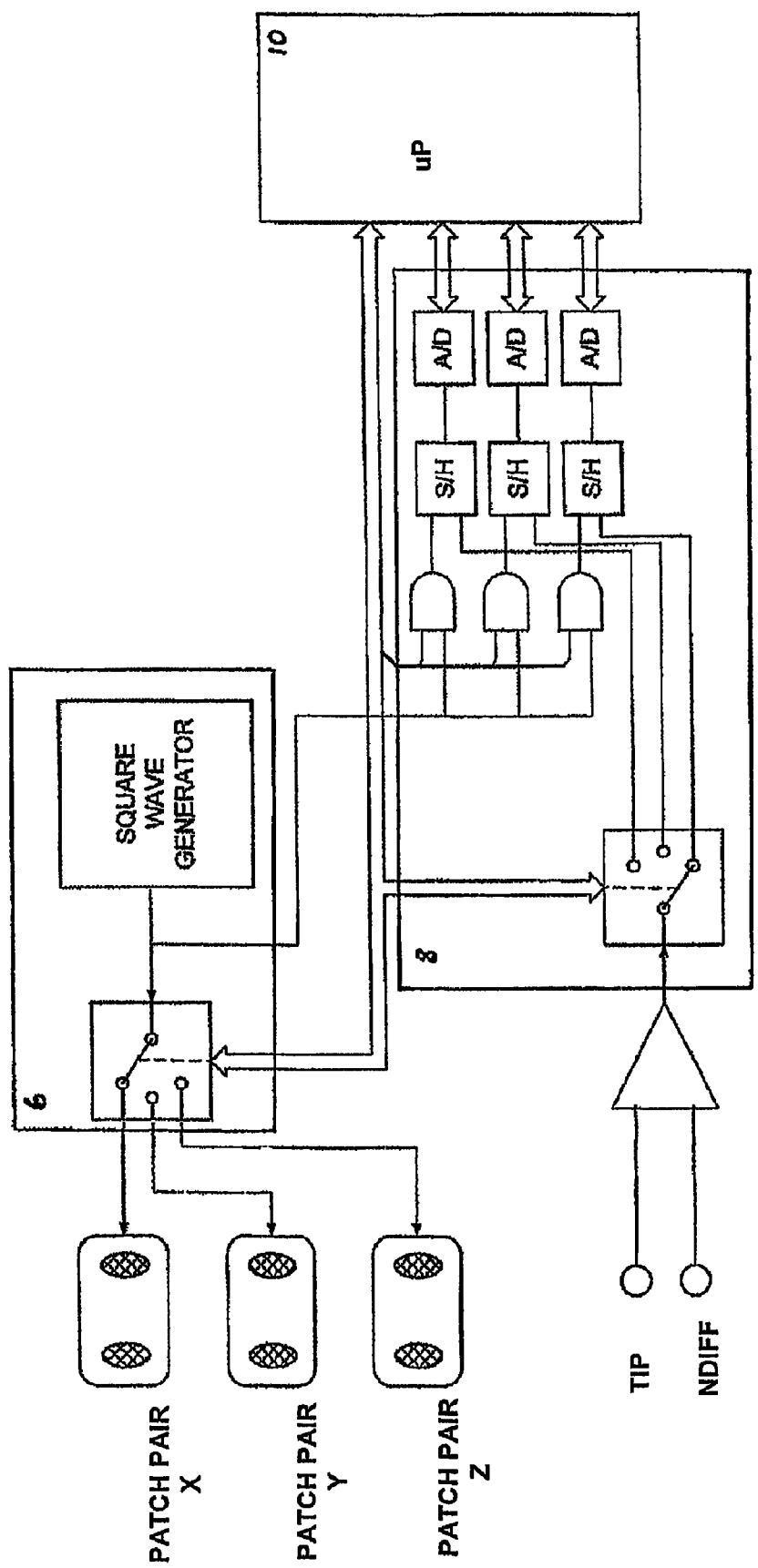
FIG. 4 shows a more detailed block diagram of the medical system according to the present invention.

As illustrated in e.g. FIG. 4 an amplifier is connected to the electrode leads that will acquire the resulting signals, caused by the electric fields within the body and by the tissue movements. Since alternating voltages have been used, the resulting signal is a modulated alternating signal that needs to be demodulated in order to obtain the signals, which carry information about heart wall movements. This task will be performed by the signal processing and A/D conversion means (see FIG. 3). The above-mentioned two means 6, 8 are controlled by the control means 10, that preferably includes a microprocessor. The control means will control when the switches of the voltage generators will be connected to respective patch pair. The microprocessor will also receive the A/D-converted data from the signal receiving means 8, and will thus know from which patch pair the actual signal emanates. In that way the signals, designated X, Y and Z in FIG. 3, which represent the information about e.g. heart wall movements, will be identified. That information will then be used e.g. to perform AV-delay optimization, that e.g. may be achieved by the microprocessor in the control means.

With references to FIG. 4, a detailed block diagram of the device is illustrated. In the figure is shown a square wave voltage generator in the excitation means 6 that is the source for the generation of the three electric fields inside the body. It typically has a frequency of a couple of kHz, preferably 10 kHz. The voltage will be sequentially distributed to the three pairs of patches by a multiplexer, which switching is controlled by the control means.

In a preferred set-up, using 10 kHz as excitation frequency of the square wave voltage generator and, preferably, using a 100 Hz switching frequency of the multiplexer, each patch pair, in a three patch pair system, will be active during approximately 3 ms and a total cycle for exciting all three patch pairs is then 9 ms. Thus, the 10 kHz excitation frequency results in 30 periods per each 3 ms activation slot of a patch pair.

An electrode of a pacemaker lead inside the body will collect potentials which are directly correlated with the square wave voltage and the movements of the electrodes of the lead. The signals from the lead will show a square wave shape modulated by electrode movements and switching of the electric fields. After amplification the lead signals will be fed to a multiplexer, which switching is in synchronism with the switching of the electric fields. In that way signals from respective electric field direction are separated. The signals are applied to the input of three sample and hold circuits in the signal receiving unit 8. The nature of the signals are still square wave shaped. The transfer to a slowly varying signal is accomplished by activating each sample and hold circuit synchronously with the square wave voltage.

It may be preferable to insert a small time delay before the sample and hold circuit samples, in order to let the raw data signals reach their asymptotic levels.

Correct gating of the square wave voltage signal is accomplished by AND-gates receiving information on which electric field is active at each time. Each sample and hold circuit is connected to an analog and digital converter. The control means is preferably embodied by the microprocessor (μm). The microprocessor will then control the electric field multiplexer since it includes information regarding which electric field is active and also from which A/D-converter appropriate information may be received.

The microprocessor then receives information of how the electrodes move inside the body. The electrodes are normally attached to the heart walls and will thus follow the movements of those. This may be further utilized by the microprocessor for varying parameters of the pacemaker/ICD, which will result in different heart muscle activities. The movement of the heart muscle may be obtained in that way. If the electrodes are placed in such a way that they deliver signals which will be representative of heart wall contractions the microprocessor may carry out a test by varying, e.g. the AV-delay, and simultaneously notice which delay resulted in the most favorable heart wall movement. Other parameters may be VV-delay and stimulation rate.

It is not necessary that the control means is arranged to control any therapy directly. The functions may be used for observation only during other forms of therapies delivered to the patient or simply by the patient performing various body activities. Information of the results thereof may be transmitted to an external device via e.g. a wireless communication link.

Figure 5:
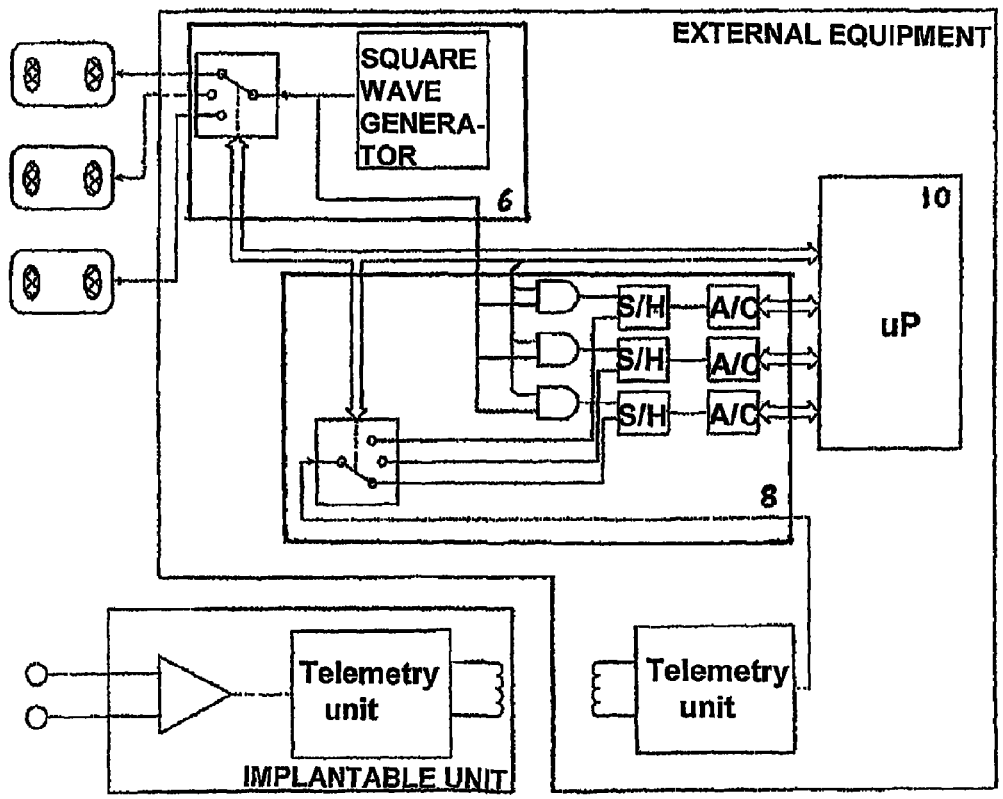
FIG. 5 shows a block diagram of a second preferred embodiment of the present invention.

FIG. 5 shows a schematic block diagram of another preferred embodiment of the present invention especially applicable at follow-up procedures. In this embodiment the detected voltage potential difference is wirelessly communicated from the implantable unit, using e.g. conventional telemetry, to the external medical system. The function of the external medical system (external equipment) in FIG. 5 is the same as in the system described above in connection with FIG. 4.

Figure 6:
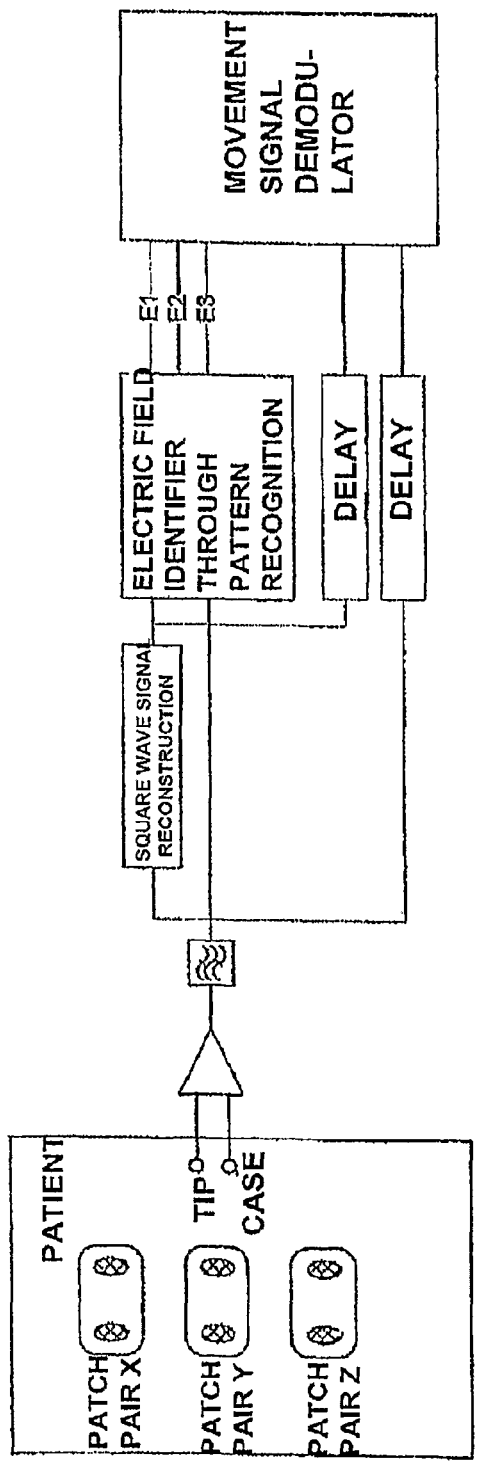
FIG. 6 shows a block diagram of an alternative embodiment of the present invention.

FIG. 6 shows a schematic block diagram of an alternative embodiment of the present invention that illustrates the detection and identification of the three electric fields that are necessary for demodulation of the square wave signal, e.g. for obtaining heart wall movements.

The reconstruction of the square wave from the raw signals obtained from inside the patient is improved by using a band-pass filter enhancing the known frequency of the square wave. Phase-locked loops are circuits known to perform such actions. The identification of the electric fields may be performed in a number of ways, by giving each field a unique signal pattern, e.g. by inserting a short period at the end of each period of each field that may leave an empty space during which no square waves are delivered. This may start a test period, during which the pulse pattern of the next square waves will be correlated with a pre-known pattern, unique for each field. The identification of each electric field will therefore be delayed. The reconstructed square wave and the raw signals must be delayed to the same degree. In this way all necessary signals are at hand for obtaining the heart wall movement signals as have been presented in relation with the other embodiments.

In the above embodiments the detecting electrode and the reference electrode are separate from the electric field generating electrodes. It is naturally also possible to use one or many of the electrodes of the electric field generating electrodes as reference electrode. A person skilled in the art would easily arrange a multiplexing circuitry to make the necessary connections in order to use one of those electrodes as a reference electrode.

Figure 7:
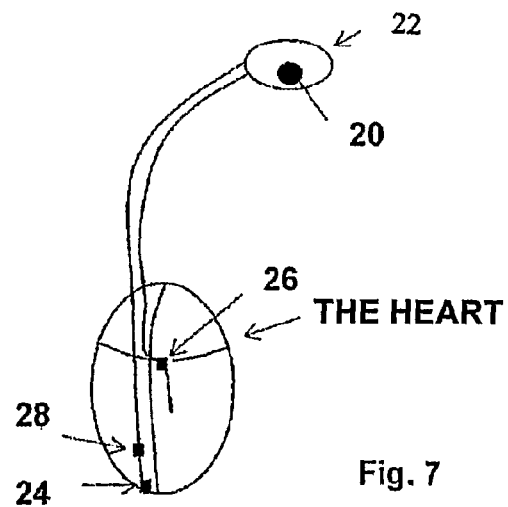
FIG. 7 shows a principal set-up of another alternative embodiment of the present invention.

According to another alternative embodiment, schematically illustrated in FIG. 7, only one electrode pair is used to create the electric field and in this embodiment the electric field is created between two implanted electrodes, e.g. between an electrode 20 at the stimulator housing 22 and a ventricular tip electrode 24 positioned in the lower part of the right ventricle. The detection electrode may then be e.g. a coronary sinus electrode 26 arranged between the housing and the ventricular tip electrode. The potential difference signal, obtained by such an invasive set-up, measured between the detection electrode and a ventricular ring electrode 28 being the reference electrode, may then, after an appropriate processing, be used to monitor the movement of the valve plane.

Below is generally described how the medical system according to the present invention may be used in connection with an implantable heart stimulating system.

In a conventional set-up of an implantable heart stimulating system an LV lead is positioned in a coronary vein on e.g. the left lateral heart wall. Another lead is placed in the right ventricle. In addition, an atrial lead may also be present. The leads are arranged such that their electrodes will follow the movements of the heart walls. This may be accomplished by screwing the RV-lead into the free RV-wall or septum or by creating a loop inside the right ventricle making the ring— electrode pressing against the wall. An alternative way is obtained by inserting a pre-bent stylet into the lead forcing the ring-electrode to adhere to the wall.

Stimulation pulses will be applied to the stimulating electrodes in the heart separated by different AV- and/or VV-delays as is common practice in the art.

The left and right heart wall movements will then be tracked and observed using the system according to the present invention.

The AV- and VV-delay settings may now be changed and set to optimal values by the physician according to gained experience of the timings that result in optimal hemodynamics.

A simplified way to perform this is to change AV/VV-delays in order to get simultaneous wall movements.

The positions of the stimulating electrodes may have a large impact on the hemodynamic performance. A change in stimulating electrode position may demand another VV-delay for optimal pacing. The physician should therefore test different delays for different stimulating sites.

Since also the dynamics of the heart walls are measurable, a measure of the contractility may be obtained. The contractility is influenced both by AV- and VV-delays, and may thus also be used for optimal settings of those parameters.

The movement of the heart walls during VV-pacing may vary from one position to another. In many cases synchronized RV- and LV-contractions result in maximum contractility or maximum heart muscle movements. The measurements of heart wall movements according to this invention may be applied in this situation. With electric fields from external patches, heart wall movements in three directions may be obtained. The movement data will be picked up from the point in time where the most forceful contractions occur. The three movement components can be processed in different ways and with varying degrees of computational demands. It may be sufficient to just pick one of them or use the sum. If needed and if the computational resources are at hand, the vector sum of the three vectors may be calculated.

The optimum VV-delay will be found by bi-ventricular stimulation, stepping through a range of VV-delays under observation of heart wall movements and picking the highest value. In a one dimensional movement direction the reliability of the measurement is lower, but the same procedures still apply.

Preferably, it is sufficient to measure heart wall movements during a limited portion of the heart cycle. The period of interest starts with the stimulation pulse(s) and ends after about 100-200 ms.

By combining the heart wall movement pattern with a conventional surface ECG further parameters may be determined which can be used to optimize the settings of the heart stimulator, among these parameters may be mentioned e.g. the pre-ejection period (PEP), Left ventricular ejection time (LVET) and electromechanical systole (EMS).

Although modifications and changes may be suggested by those skilled in the art, it is the intention of the inventors to embody within the patent warranted heron all changes and modifications as reasonably and properly come within the scope of their contribution to the art.

We claim as our invention:

1. Medical system, comprising:
   an implantable medical device configured for in vivo implantation in a subject, said implantable medical device being configured to provide an in vivo medical therapy to the subject according to therapy parameters set by a control unit in the implantable medical device;
   a predetermined number of electrode pairs connected to said implantable medical device and configured to be arranged at or within the subject;
   electric field excitation signal generators in said implantable medical device, connected to the electrodes, that apply alternating voltage excitation signals at a preset frequency to the electrodes of each electrode pairs to generate an electric field through the heart between the electrodes of the respective electrode pairs;
   a signal receiver in said implantable medical device that receives a signal representing the voltage potential difference between a voltage potential of at least one of the heart electrodes used as detecting electrode and a reference electrode, a voltage potential being related to the generated electric field, and that thereafter generates a potential difference signal, representing said voltage potential difference;
   a signal controlling and processing unit in communication with said signal receiver, that is provided with and processes the detected potential difference signal in order to determine cardiac parameters representing heart activity; and
   said control unit also being in communication with said signal controlling and processing unit and being supplied with said cardiac parameters by said signal controlling and processing unit, said control unit being configured to set or adjust said therapy parameters dependent on said cardiac parameters.

2. A medical system according to claim 1, comprising a first switch that, under the control of the controlling and processing unit, switches between electrode pairs such that the generated electrical fields from different electrode pairs are generated separate from each other.

3. A medical system according to claim 2, wherein the signal receiving unit includes a second switch that, under the control of the controlling and processing unit, switches in synchronism with the switching of the first switch such that a correlation between the received voltage potential difference signal and the respective electric field generating electrode pair is achieved.

4. A medical system according to claim 1, wherein said electrodes are surface electrodes.

5. A medical system according to claim 1 comprising three pairs of electrodes.

6. A medical system according to claim 5 wherein an alternating voltage applied to the surface electrodes is sequentially distributed to the three pairs of surface electrodes.

7. A medical system according to claim 1, wherein the alternating voltage excitation signals have a square wave pulse form and a frequency in the interval 1-10 kHz.

8. A medical system according to claim 1, wherein said signal receiving unit is directly connected to electrode leads during an implantation procedure.

9. A medical system according to claim 1, wherein said signal receiving unit is configured to receive signals from tip electrodes at the distal end of the electrode lead.

10. A medical system according to claim 1, wherein said signal receiving unit is configured to receive signals from an electrode surface at the heart stimulator housing.

11. A medical system according to claim 1, comprising a transmitter that wirelessly transmits the voltage potential difference sensed by the heart stimulator electrodes from the implantable stimulator to the signal receiving unit.

12. A medical system according to claim 1, wherein the signal receiving unit includes sample and hold circuits activated in dependence of the generated alternating voltages to generate a slowly varying signal representing the movement of the detecting electrode.

13. A medical system according to claim 1, wherein said heart activity parameters relate to the VV- and/or AV-delay.

14. A medical system according to claim 1, wherein said parameters relate to the position of the lead electrodes.

15. A medical system according to claim 1, wherein heart activity relates to heart wall movement.

16. A medical system according to claim 1, wherein said heart activity relates to movements of the heart valve plane.

17. A medical system according to claim 1, wherein said heart activity parameters are used to optimize the operation of the heart stimulator.

18. Medical system comprising:
   an implantable medical device configured for in vivo implantation in a subject, said implantable medical device being configured to provide an in vivo medical therapy to the subject according to therapy parameters set by a control unit in the implantable medical device;
   a predetermined number of electrode pairs connected to said implantable medical device and configured to be arranged at or within the subject;
   electric field excitation signal generators in said implantable medical device, connected to the electrodes, that apply alternating voltage excitation signals at a preset frequency to the electrodes of each electrode pairs to generate an electric field through the heart between the electrodes of the respective electrode pairs;
   an extracorporeal signal receiver;
   a telemetry system comprising telemetry components in said implantable medical device and in said signal receiver, said telemetry system being configured to communicate a signal from said implantable medical devices to said extracorporeal signal receiver that represents the voltage potential difference between a voltage potential of at least one of the heart electrodes used as detecting electrode and a reference electrode;
   the voltage potential being related to the generated electric field;
   said signal receiver being configured to generate a potential difference signal, representing said voltage potential difference;
   an extracorporeal signal controlling and processing unit in communication with said extracorporeal signal receiver, that is provided with and processes the detected potential difference signal in order to determine and display cardiac parameters representing heart activity; and said control unit also being in communication via said telemetry system with said signal controlling and processing unit and being supplied with said cardiac parameters by said signal controlling and processing unit, said control unit being configured to set or adjust said therapy parameters dependent on said cardiac parameters.

* * * * *